(12) United States Patent
Kojima et al.

(10) Patent No.: US 7,981,690 B2
(45) Date of Patent: Jul. 19, 2011

(54) METHOD OF ASSAYING ANTIGEN AND KIT TO BE USED THEREIN

(75) Inventors: Ryo Kojima, Koriyama (JP); Yoshiro Sato, Koriyama (JP); Katsuhiro Katayama, Koriyama (JP)

(73) Assignee: Nitto Boseki Co., Ltd., Fukushima-Shi (JP)

( * ) Notice: Subject to any disclaimer, the term of this patent is extended or adjusted under 35 U.S.C. 154(b) by 568 days.

(21) Appl. No.: 12/083,877

(22) PCT Filed: Nov. 10, 2006

(86) PCT No.: PCT/JP2006/322486
§ 371 (c)(1),
(2), (4) Date: Apr. 21, 2008

(87) PCT Pub. No.: WO2007/058129
PCT Pub. Date: May 24, 2007

(65) Prior Publication Data
US 2010/0151587 A1 Jun. 17, 2010

(30) Foreign Application Priority Data
Nov. 18, 2005 (JP) .................................. 2005-333597

(51) Int. Cl.
*G01N 33/53* (2006.01)
*G01N 33/543* (2006.01)
*G01N 33/566* (2006.01)

(52) U.S. Cl. .......... 436/501; 435/7.1; 436/524; 436/533

(58) Field of Classification Search .................. None
See application file for complete search history.

(56) References Cited

U.S. PATENT DOCUMENTS

| 4,732,863 A * | 3/1988 | Tomasi et al. ................ 424/1.53 |
| 4,868,106 A | 9/1989 | Ito et al. |
| 5,858,803 A | 1/1999 | Schenk et al. |
| 2003/0003602 A1 | 1/2003 | Vogt et al. |
| 2005/0129616 A1 | 6/2005 | Salcedo et al. ................ 424/1.49 |

FOREIGN PATENT DOCUMENTS

| JP | 62-90538 | 4/1987 |
| JP | 2-64459 | 3/1990 |
| JP | 9-304389 | 11/1997 |
| JP | 11-344492 | 12/1999 |
| JP | 2001-91516 | 4/2001 |
| JP | 2002-296281 | 10/2002 |
| JP | 2004-196777 | 7/2004 |
| WO | WO2004/013287 | 2/2004 |
| WO | WO 2004/060041 A2 | 7/2004 |

OTHER PUBLICATIONS

H. Toyama, et al.; *The Journal of Clinical Laboratory Instruments and Reagents*; vol. 21; No. 3; 1998; pp. 251-257 and Two Cover Sheets (9 Sheets total.).
Supplementary European Search Report dated May 25, 2009.

* cited by examiner

*Primary Examiner* — Mark Shibuya
*Assistant Examiner* — Galina Yakovleva
(74) *Attorney, Agent, or Firm* — Kratz, Quintos & Hanson, LLP

(57) ABSTRACT

By using an antibody which is covalently bonded to a water soluble polymer as an antibody to be used in a competitive immunoagglutination assay in a homogeneous system, a protein antigen at a high concentration can be accurately assayed in an undiluted system without resorting to dilution.

17 Claims, 2 Drawing Sheets

METHOD OF ASSAYING ANTIGEN AND KIT TO BE USED THEREIN

TECHNICAL FIELD

The present invention relates to a method of assaying an antigen and a kit to be used therein. More particularly, the present invention relates to a method of assaying an antigen in a sample by a competitive immunoagglutination assay in a homogenous system, wherein the method is suitable for assaying an antigen such as albumin, a protein present in a biological sample at a high concentration, and to a kit to be used therein.

BACKGROUND ART

A turbidimetric immunoassay such as a latex turbidimetric immunoassay is known as one of methods for assaying a protein present in a blood sample. Since such methods are capable of assaying a great number of samples in a short period of time, they are widely used in the field of laboratory tests. However, various problems arise when these methods are used in an attempt to assay a protein present in blood at a high concentration of about $10^{-3}$M, such as albumin. Specifically, in that case, the operation before assay is complicated, because blood analyte collected as a sample must be diluted before use. Further, such methods require the use of a large amount of an antibody as a measuring reagent, which makes the measuring reagent more costly. Still further, a prozone phenomenon easily occurs, and consequently the assay in a high concentration region may be impossible. As a result, the assay of protein in an undiluted system by the turbidimetric immunoassay has not yet been in practical use.

Meanwhile, in connection with the turbidimetric immunoassay, a competitive immunoagglutination assay in a homogenous system is known as one of immunoassays (Patent Documents 1, 2 and 3). The competitive immunoagglutination assay in a homogeneous system is a method for quantitatively determining an antigen to be assayed based on the degree of agglutination as a result of an antigen-antibody reaction between an antigen carried on fine particles and an antibody, the method comprising the steps of; mixing a sample containing an antigen to be assayed, an antibody against the antigen, and fine particles carrying an antigen capable of binding to the antibody; and competing an antigen-antibody reaction of the antibody between the antigen in the sample and the antigen carried on fine particles. This method has an advantage that an antigen at a low concentration can be assayed through various efforts, and studies have thus been made from this perspective. However, in the case of using this method to assay a protein at a high concentration, in generating calibration curves, measurement blanks exceed a measurable upper limit when the concentration of the protein to be assayed is 0. Accordingly, the assay becomes impossible. Therefore, almost no study has been made to assay a protein at a high concentration by using this method, and in consequence, the method has yet been in practical use.

Patent Document 1: JP-A-57-206859
Patent Document 2: JP-A-58-500874
Patent Document 3: JP-A-2002-296281

DISCLOSURE OF THE INVENTION

Accordingly, the present invention is directed to providing a method of assaying an antigen in an undiluted system using a competitive immunoagglutination assay in a homogeneous system, which conventionally has been hardly used for assaying an antigen at a high concentration, and to providing a kit to be used for the method of assay.

Under such circumstances, in order to solve the problems, the present inventors have made studies on assaying an albumin in a sample by a competitive immunoagglutination assay in a homogeneous system, to which consideration has been hardly given from the aspect of assaying a protein at a high concentration. As a result, it has surprisingly been found that an albumin at a high concentration can be accurately assayed in an undiluted system without resorting to dilution when an antibody which is covalently bonded to a water soluble polymer is used as an antibody for a competitive immunoagglutination assay in a homogeneous system. The present invention has thus been accomplished.

Accordingly, the present invention relates to a method of assaying an antigen by a competitive immunoagglutination assay in a homogeneous system, comprising the steps of; mixing a sample containing an antigen to be assayed, an antibody against the antigen, and fine particles carrying the same antigen as the antigen to be assayed or an analogue of the antigen, which analogue may undergo an antigen-antibody reaction with the antibody; competing an antigen-antibody reaction of the antibody between the antigen in the sample and the same antigen as the antigen to be assayed or the analogue of the antigen, both of which are carried on fine particles; and quantitatively determining the antigen to be assayed based on the degree of agglutination as a result of the antigen-antibody reaction of the antibody with the same antigen as the antigen to be assayed or the analogue of the antigen, both of which are carried on fine particles characterized in that the antibody is covalently bonded to a water soluble polymer.

Further, the present invention relates to a kit for assaying an antigen, including an antibody against an antigen to be assayed, which antibody is covalently bonded to a water soluble polymer, and fine particles carrying the same antigen as the antigen to be assayed or an analogue of the antigen, which analogue may undergo an antigen-antibody reaction with the antibody.

The method of assay according to the present invention makes it possible to carry out an immunoassay of an antigen, a protein present in a biological sample at a high concentration, such as albumin, without developing a prozone phenomenon, as well as without diluting a sample, by using costly antibody serving as measuring reagent in small quantity.

BEST MODE FOR CARRYING OUT THE INVENTION

Figure 1:
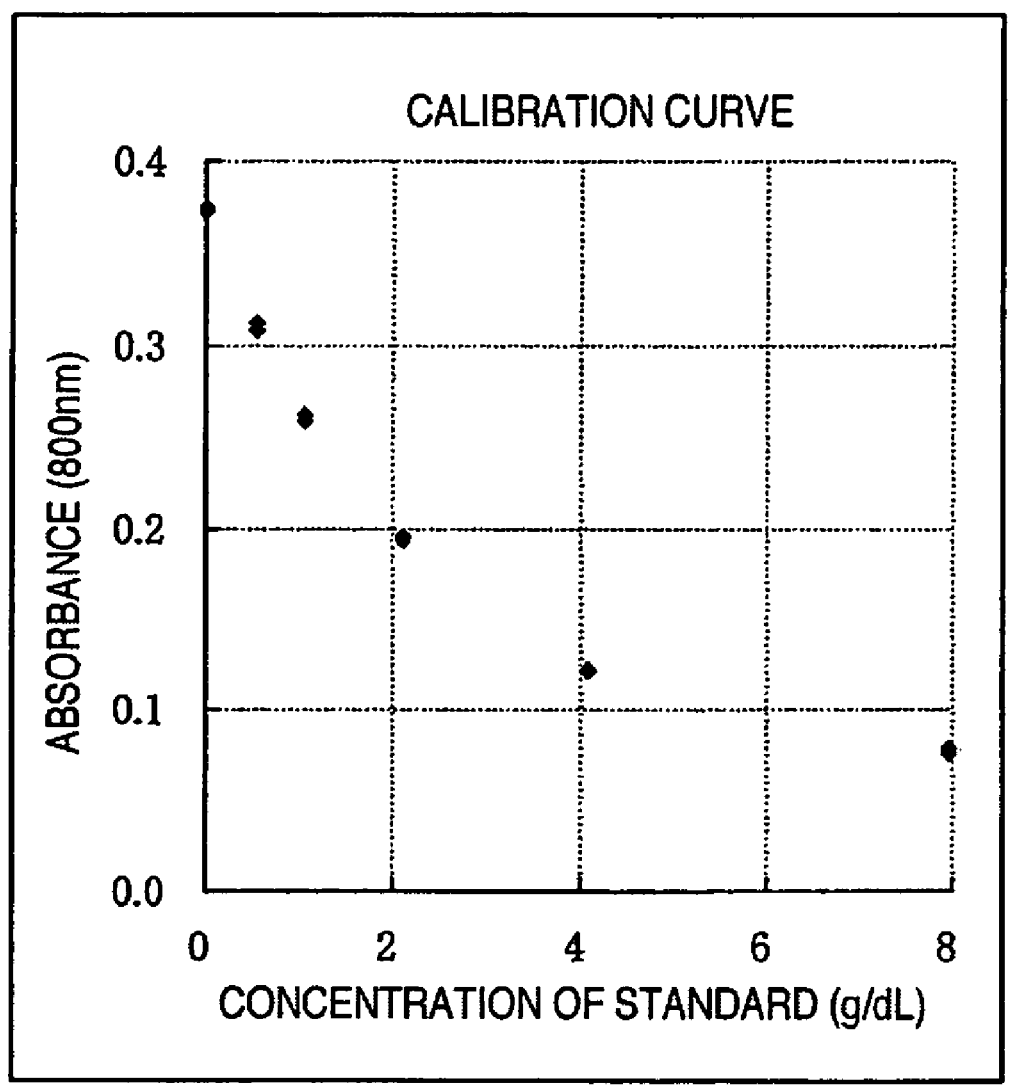
FIG. 1 shows a calibration curve prepared by the method of assay according to the present invention.

The method of assay according to the present invention is based on a principle that, in a competitive immune reaction, any one of reaction reagents or products has turbidity while other components are dissolved in water. The principle will hereinafter be illustrated.

The following objects are used to be mixed as a reaction reagent: (i) an antigen derived from a sample; (ii) a conjugate of the same antigen as the antigen of (i) or an analogue of the antigen thereof, and fine particles; and (iii) an antibody as a reagent. The antigen of (i), the conjugate of (ii) and the antibody of (iii) are all soluble in water or capable of homogeneous dispersion. They are then mixed to undergo an antigen-antibody reaction, which causes competitive formation of the following antigen-antibody complexes: (iv) a complex of the conjugate of (ii) and the antibody of (iii); and (v) a complex of the antigen of (i) and the antibody of (iii). The complex of (iv) is insoluble in water, which causes turbidity, whereas the complex of (v) is soluble in water. Therefore, as more complexes of (iv) are formed, turbidity in a reaction solution increases.

In this competitive reaction, the antigen of (i) reacts with the limited amount of antibody of (iii) competitively against the conjugate of (ii) and, thereby reducing the amount of the resulting insoluble complex of (iv) while lowering turbidity in a reaction solution. Therefore, as the concentration of the antigen in a sample is higher, the turbidity in the reaction solution is smaller. The antigen in a sample can thus be assayed based on the degree of turbidity.

Meanwhile, in the competitive immune reaction, when the concentration of the antigen of (i) in a sample is high, the concentration of the conjugate of (ii) and the antibody of (iii) must be increased. In this case, since a large amount of the complex of (iv) is formed, the turbidity becomes too dense, which makes the measurement more likely to fail.

In the present invention, an antibody which is covalently bonded to a water soluble polymer is used as an antibody serving as a reagent for inhibiting an antigen-antibody reaction, so that the turbidity of reaction system can be reduced to a measurable level.

In the present invention, it is preferable that an antigen to be assayed is a substance present in a biological sample and particularly a protein present in a biological sample at a high concentration. Specifically, albumin, IgG, IgA and IgM are preferable, and albumin and IgG are more preferable. Of these substances, albumin is most preferable, because the present invention enables quantitative determination by an immunoassay without diluting a sample, although such quantitative determination has not yet been in practical use in the field of laboratory tests. In the present invention, a sample is, for example, a liquid sample derived from living organisms. Examples of such include plasma, serum or urine.

An antibody used in the present invention is an antibody against an antigen to be assayed. As long as it is the antibody described above, both polyclonal antibody and monoclonal antibody may be used.

In the present invention, an analogue of an antigen is a substance that is structurally similar to the antigen and is capable of binding through an antigen-antibody reaction with an antibody.

In the present invention, fine particles typically employed for immune agglutination can be used as they are. The most popular fine particles are latex particles. The fine particle having a particle size ranging from 0.01 to 0.5 micron is generally used.

In the present invention, common methods such as a physical adsorption method or a covalent binding method based on hydrophobic interaction can be used to have the same antigen as the antigen to be assayed or an analogue thereof carried on fine particles.

Examples of the water soluble polymer to which an antibody is covalently bonded include polyethylene glycol, polyvinyl alcohol, dextran, poly(N-vinyl pyrolidone), polyacryl amide, polyacroylmorphorine or polyoxazoline, poly(N-2-(hydroxypropyl) metacryl amide). Of these polymers, polyethylene glycol and polyvinyl alcohol are preferable, provided that the polymers are water soluble at room temperature.

Polyethylene glycol are not particularly limited and include polyethylene glycol homopolymer, polyoxyethylated polyol, polyoxyethylated glycerin, polyoxyethylated sorbitol, or polyoxyethylated glucose, as long as the polymers have a repeating unit of —$CH_2CH_2O$—. It is to be noted that one end of polyethylene glycol may be substituted with an alkyl group having 1 to 4 carbon atoms, preferably 1 to 2 carbon atoms.

Preferred examples of polyethylene glycol include unsubstituted polyethylene glycol, monomethyl polyethylene glycol, or polyoxyethylated glycerin. Of these polyethylene glycol, monomethyl polyethylene glycol is more preferable.

A conventional method of covalently binding peptide or protein to a water soluble polymer can be employed to covalently bind an antibody to a water soluble polymer such as polyethylene glycol. For example, a water soluble polymer and an antibody can be covalently bonded by: binding 4-hydroxy-3-nitrobenzenesulfonate ester or N-hydroxy succinimide ester (N-hydroxy succinate imide) of carboxylic acid, or p-nitrophenyl carbonate or 2,4,5-trichrol phenyl carbonate to the end of a water soluble polymer such as polyethylene glycol, through a spacer as desired; reacting the resulting substance with an amino group in an antibody; and forming an amide bond or an urethane bond.

The average molecular weight of a polymer is selected, for example, in accordance with an antibody to be used. However, in general, the average molecular weight thereof is preferably about 200 to 10,000, more preferably 300 to 4,000. When the molecular weight is too low, the inhibition of an antigen-antibody reaction may be insufficient. Meanwhile, when the molecular weight is too high, an antibody which is covalently bonded to a water soluble polymer may be hard to melt in water.

In the present invention, as a method for quantitatively determining the degree of agglutination, a method for measuring the resulting turbidity by absorbance is generally used. However, it can also be implemented by observing aggregate with the naked eyes or by counting the number of non-agglutinated particles.

Specifically, the method of assay according to the present invention can be conducted as follows:

It begins by preparation of reagents including a first reagent wherein fine particles carrying the same antigen as an antigen to be assayed or an analogue of the antigen are homogeneously dispersed in a buffer such as a phosphate buffer, and a second reagent wherein an antibody covalently bonded to a water soluble polymer is dissolved in a buffer such as a phosphate buffer. Then, the first and second reagents are added to a sample containing the antigen to be assayed using an automated analyzer, and an antigen-antibody reaction is carried out to obtain the agglutination rate, which is measured as an amount of change in absorbance at a wavelength of, for example, 800 nm by a two-point end method. The desired antibody in the sample can be quantitatively determined by the measurements thus obtained with a reference to a previously generated calibration curve using standard samples of known antigen concentrations.

To achieve the quantitative determination according to the present invention, a kit for quantitatively determining an antigen including an antibody against an antigen, which antibody is covalently bonded to a water soluble polymer, and fine particles carrying an antigen or an analogue of the antigen can be used.

The antibody and the fine particles as described in the method of quantitative determination can be used as an antibody against an antigen, which antibody being covalently bonded to a water soluble polymer, and as fine particles carrying an antigen or an analogue of the antigen.

The following examples illustrate the present invention and are not intended to limit the scope of the present invention.

EXAMPLE 1 and COMPARATIVE EXAMPLE 1

Consideration of PEGylated Antibody

The following experiment was conducted for the purpose of controlling an antigen-antibody reaction by binding an antibody to PEG (polyethylene glycol). For comparison, the same experiment was conducted by adding an immune response inhibitor such as sodium chloride to a non-PEGylated antibody.

1) Preparation of Human Albumin-Sensitized Latex Particles

The adsorption of albumin to latex particles was conducted as follows:

To 100 ml of a 1% suspension of polystyrene latex particles having a particle size of 67 nm was added 100 ml of a solution prepared by dissolving human serum albumin (produced by The Scripps Research Institute) in a phosphate buffer to a concentration of 10%. The resulting mixture was stirred at room temperature for 2 hours, and then centrifuged at 18,000 rpm for 3 hours to remove supernatant, thereby obtaining precipitate. The precipitate thus obtained was suspended in 100 ml of a phosphate buffer, and further centrifuged to remove unadsorbed excess human serum albumin therefrom. Then, the resulting precipitate was suspended in 20 ml of a phosphate buffer, and then subjected to ultrasonic treatment to fully disperse latex particles. The suspension of human albumin-sensitized latex particles with a latex concentration of 5% was refrigerated.

2) Preparation of PEGylated Anti-Human Albumin Goat Serum γ Fraction

A reagent (produced by NOF Corporation, trade name: SUNBRIGHT ME-020CS, PEG molecular weight of 2,000) represented by the formula $CH_3O(CH_2CH_2O)nCOCH_2CH_2CO$—OSu (wherein OSu is a residue having H of HOSu (N-hydroxysuccinic imide) removed therefrom) was used as a PEGylating reagent. An antibody was PEGylated as follows:

As an antibody, 10 ml of a solution of anti-human albumin goat serum γ fraction (produced by International Immunology Corporation, total protein concentration of 6.5 g/dL) was used. In addition to the antibody, 1 g of a PEGylating reagent was added to and dissolved in 10 ml of a phosphate buffer so as to prepare a PEGylated solution. Then, the antibody solution and the PEGylated solution were mixed at a mixing ratio of 1:1 and allowed to stand at room temperature overnight to obtain a PEGylated antibody with a protein concentration of 3.25 g/dL 3) Preparation of Serum Albumin Measuring Reagent Latex particles having albumin adsorbed therein and a PEGylated antibody were used to prepare first and second reagents.

The first reagent was used as a suspension at a latex concentration of 4%, prepared by adding 5 ml of a phosphate buffer to 20 mL of a suspension of human albumin-sensitized latex particles. The second reagent was used as a solution at a protein concentration of 1.3 g/dL, prepared by adding 15 mL of a phosphate buffer to 10 mL of a solution of PEGylated anti-human albumin goat serum γ fraction at a protein concentration of 3.25 g/dL. The resulting solution has a γ fraction concentration of 20%.

In addition, a control reagent was prepared by diluting non-PEGylated anti-human albumin goat serum γ fraction with a phosphate buffer to a protein concentration of 1.3 g/dL.

Furthermore, as Comparative Example 1, a γ fraction solution at a protein concentration of 1.3 g/dL was prepared by adding 1,000 mM of sodium chloride for inhibiting an immune reaction to non-PEGylated anti-human albumin goat serum γ fraction.

A sample was prepared by diluting serum of a known albumin concentration with physiological saline accordingly.

The compositions of each reagent are described as follows:

Composition of Phosphate Buffer

| | |
|---|---|
| Sodium dihydrogenphosphate dihydrate | 20 mM pH 7.50 |
| EDTA · 2Na | 1 mM |

Composition of First Reagent

| | |
|---|---|
| Sodium dihydrogenphosphate dihydrate | 20 mM pH 7.50 |
| EDTA · 2Na | 1 mM |
| Human albumin-sensitized latex particles | 4% (v/v) |

Composition of Second Reagent

| | |
|---|---|
| Sodium dihydrogenphosphate dihydrate | 20 mM pH 7.50 |
| EDTA · 2Na | 1 mM |
| PEGylated anti-human albumin goat serum γ fraction (protein concentration) | 1.3 g/dL |

Composition of Second Reagent (Control Reagent)

| | |
|---|---|
| Sodium dihydrogenphosphate dihydrate | 20 mM pH 7.50 |
| EDTA · 2Na | 1 mM |
| Anti-human albumin goat serum γ fraction (untreated) (protein concentration) | 1.3 g/dL |

Composition of Second Reagent (Comparative Example 1)

| | |
|---|---|
| Sodium dihydrogenphosphate dihydrate | 20 mM pH 7.50 |
| EDTA · 2Na | 1 mM |
| Anti-human albumin goat serum γ fraction (untreated) (protein concentration) | 1.3 g/dL |
| Sodium Chloride | 1,000 mM |

4) Measurement of Absorbance

A Hitachi 7170S type automated analyzer was used for the measurement of serum albumin, in which 270 μL of each of the first and second reagents were reacted with 2 μL of serum as a sample. Then, the amount of change in absorbance between the photometric point 19 and the photometric point 30 (corresponding to 1 to 4 minutes after adding the second reagent) was measured at a wavelength of 800 nm by a two-point end method.

5) Measurement Results

The amount of change in absorbance in the case of measuring serum albumin by using the above-described reagents is shown in Table 1.

TABLE 1

Amount of change in absorbance of serum albumin
by Hitachi 7170S type automated analyzer Amount of change in absorbance at 800 nm

| Concentration of serum albumin (g/dL) | Example 1: PEGylated antibody | Control Reagent: non-PEGylated antibody | Comparative Example 1: non-PEGylated antibody and sodium chloride |
|---|---|---|---|
| 0 | 0.3865 | Over absorbance | Over absorbance |
| 1.0 | 0.2551 | Over absorbance | Over absorbance |
| 2.0 | 0.1713 | Over absorbance | Over absorbance |
| 4.0 | 0.0955 | Over absorbance | Over absorbance |
| 6.0 | 0.0645 | Over absorbance | Over absorbance |
| 8.0 | 0.0376 | Over absorbance | Over absorbance |

As shown in Table 1, in the case of using a PEGylated antibody, the absorbance decreases as the albumin concentration increases. This is caused by a competitive reaction between an albumin in a sample and an albumin which is bonded to latex particles added to a reagent.

Furthermore, in the present invention, since an antibody used for reaction is PEGylated, the absorbance of reaction stays within a measurable level. This is believed to be caused by PEGylation of an antibody, which makes albumin that is to be bonded to an antibody undergo steric hindrance, and consequently, the absorbance is controlled properly. The present invention was the first to provide a finding that the absorbance of reaction may be freely controllable by PEGylation of an antibody, and hence being unpredictable.

Meanwhile, in the case of using a non-PEGylated antibody, the reaction between an antibody and albumin-sensitized latex particles becomes uncontrollable, and the absorbance exceeds a measurable upper limit of the automatic analyzer. Ultimately, it is impossible to perform the measurement at all. Similarly, when an immune reaction inhibitor such as sodium chloride was used, the absorbance exceeded the measurable upper limit, thereby rendering the measurement impossible.

EXAMPLE 2

Measurement of Serum Albumin

The measurement of serum albumin was performed by using latex particles having albumin adsorbed therein and a PEGylated antibody.

1) Preparation of Human Albumin-Sensitized Latex Particles

To 200 mL of a 1% suspension of polystyrene latex particles having a particle size of 67 nm was added 200 ml of a solution prepared by dissolving human serum albumin in a phosphate buffer to a concentration of 10%. The resulting mixture was stirred at room temperature for 2 hours, and then centrifuged in the same manner as in Example 1. Then, the precipitate thus obtained was suspended in 40 ml of a phosphate buffer, and then subjected to ultrasonic treatment to disperse latex particles. As described above in Example 1, the suspension of human albumin-sensitized latex particles at a latex concentration of 5% was obtained.

2) Preparation of PEGylated Anti-Human Albumin Goat Serum γ Fraction

PEGylated anti-human albumin goat serum γ fraction was prepared in the same manner as in 2) of Example 1.

3) Preparation of Reagent for Serum Albumin Measurement

Latex particles having albumin adsorbed therein and a PEGylated antibody were used to prepare first and second reagents in the same manner as in Example 1.

The first reagent was used as a suspension at a latex concentration of 4%, prepared by adding 10 mL of a phosphate buffer to 40 mL of a suspension of human albumin-sensitized latex particles. The second reagent was used as a solution at a protein concentration of 1.3 g/dL, prepared by adding 30 mL of a phosphate buffer to 20 mL of a solution of PEGylated anti-human albumin goat serum γ fraction.

The compositions of each reagent are described as follows:
Composition of First Reagent

| Sodium dihydrogenphosphate dehydrate | 20 mM pH 7.50 |
|---|---|
| EDTA · 2Na | 1 mM |
| Human albumin-sensitized latex particles | 4% (v/v) |

Composition of Second Reagent

| Sodium dihydrogenphosphate dihydrate | 20 mM pH 7.50 |
|---|---|
| EDTA · 2Na | 1 mM |
| PEGylated anti-human albumin goat serum γ fraction (protein concentration) | 1.3 g/dL |

4) Measurement of Absorbance

A Hitachi 7170S type automated analyzer was used for the measurement of serum albumin concentration, in which 270 μL of each of the first and second reagents were reacted with 2 μL of serum as a sample. Then, the amount of change in absorbance between the photometric point 19 and the photometric point 30 (corresponding to 1 to 4 minutes after adding the second reagent) was measured at a wavelength of 800 nm by a two-point end method.

The albumin concentration was calculated with reference to a calibration curve generated by using a multipoint calibration curve generating function of the analyzer, in which serum evaluated by a protein standard serum CRM 470 was used as a standard. In addition, the confirmation of correlation was conducted by using "N-assay TIA Micro Alb" (produced by Nitto Boseki Co., Ltd.) according to a TIA method as a control reagent. A serum diluted 100-fold with physiological saline was used as a sample of the reagent according to the TIA method. As described above, a Hitachi 7170S type automated analyzer was used for the measurement, which was performed according to designated parameters. The results of the measurement were multiplied by 100 to obtain serum albumin values.

5) Measurement Results

A) Calibration Curve of Assay According to the Present Invention

The amount of change in absorbance in each standard is shown in Table 2, and the calibration curve in FIG. 1.

TABLE 2

Amount of change in absorbance of each standard
by Hitachi 7170S type automated analyzer in method
of assay according to the present invention

| (Concentration of standard (g/dL) | Amount of change in absorbance at 800 nm |
|---|---|
| 0 | 0.3736 |
| 0.53 | 0.3103 |
| 1.05 | 0.2604 |
| 2.11 | 0.1946 |

TABLE 2-continued

Amount of change in absorbance of each standard by Hitachi 7170S type automated analyzer in method of assay according to the present invention

| (Concentration of standard (g/dL)) | Amount of change in absorbance at 800 nm |
|---|---|
| 4.08 | 0.1218 |
| 7.96 | 0.0873 |

As shown in Table 2 and FIG. 1, a serum sample can be assayed without resorting to dilution by controlling the amount of adsorption of albumin to latex particles, and a PEGylated antibody. Since the method of the present invention utilizes a competitive reaction, as the concentration of albumin increases, the absorbance decreases. This has made it possible to prevent a prozone phenomenon, which causes problems in measuring reagents making use of immune reaction.

In the serum albumin measurement according to the conventional immunoassay, a sample must be diluted to the measurable concentration. However, the method of the present invention enables assaying without resorting to dilution, which demonstrates that the inventive method is very useful from the aspect of accuracy and operability of sample dilution.

B) Correlation with TIA Method

Figure 2:
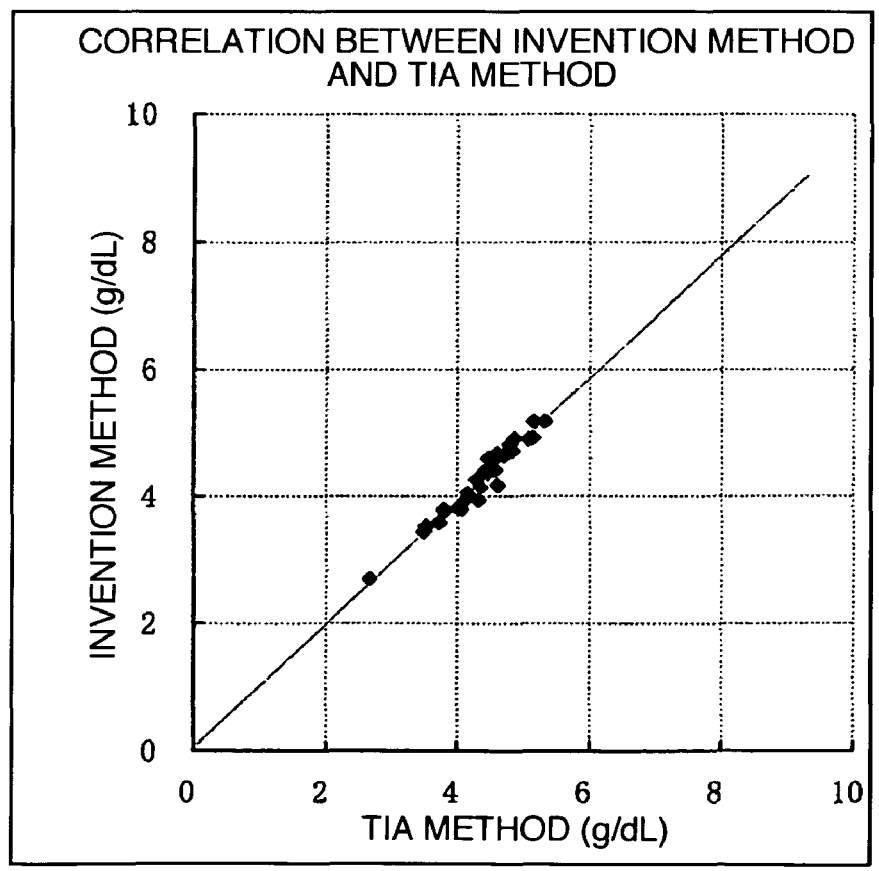
FIG. 2 shows the result of the serum albumin measurement for correlation between the method of the present invention and the TIA method.

The results of the serum albumin measurement for correlation between the method of the present invention and the TIA method are shown in FIG. 2.

The correlation was confirmed by designating the TIA method as X and the inventive method as Y. The results exhibited favorable correlation, that is, Y=0.97X+0.05 and a correlation coefficient of 0.974 (N=30). In the serum albumin measurement, the immunoassay is known as the only method for assaying serum albumin accurately. Therefore, since the present invention was confirmed to correlate with one of immunoassays, TIA, serum albumin can be accurately assayed by the method of the present invention.

INDUSTRIAL APPLICABILITY

The method of assay according to the present invention makes it possible to carry out an immunoassay of an antigen, a protein present in a biological sample at a high concentration, such as albumin, without expressing a prozone phenomenon, as well as without resorting to dilution, by using costly antibody serving as measuring reagent in small quantity.

The invention claimed is:

1. A method of assaying an antigen by a competitive immunoagglutination assay in a homogeneous system comprising the steps of:
mixing a sample containing an antigen to be assayed, an antibody against the antigen, wherein the antibody is covalently bonded to a water soluble polymer, and fine particles carrying the same antigen as the antigen to be assayed or an analogue of the antigen, which analogue is capable of undergoing an antigen-antibody reaction with the antibody;
competing an antigen-antibody reaction of the antibody between the antigen in the sample and the same antigen as the antigen to be assayed or the analogue of the antigen, both of which are carried on fine particles; and
quantitatively determining the antigen to be assayed based on the degree of agglutination as a result of the antigen-antibody reaction of the antibody with the same antigen as the antigen to be assayed or the analogue of the antigen, both of which are carried on fine particles.

2. The method of assay according to claim 1, wherein the water soluble polymer is polyethylene glycol, polypropylene glycol homopolymer, or polyvinyl alcohol.

3. The method of assay according to claim 1, wherein the water soluble polymer is polyethylene glycol.

4. The method of assay according to claim 3, wherein the antigen to be assayed is a protein present in the sample at a high concentration.

5. The method of assay according to claim 4, wherein the antigen to be assayed is an albumin.

6. The method of assay according to claim 5, wherein the assay is conducted without diluting the sample containing the antigen to be assayed.

7. The method of assay according to claim 1, wherein the antigen to be assayed is a protein present in the sample at a high concentration.

8. The method of assay according to claim 7, wherein the antigen to be assayed is an albumin.

9. The method of assay according to claim 8, wherein the assay is conducted without diluting the sample containing the antigen to be assayed.

10. The method of assay according to claim 2, wherein the antigen to be assayed is a protein present in the sample at a high concentration.

11. The method of assay according to claim 10, wherein the antigen to be assayed is an albumin.

12. The method of assay according to claim 11, wherein the assay is conducted without diluting the sample containing the antigen to be assayed.

13. The method of assay according to claim 1, wherein the assay is conducted without diluting the sample containing the antigen to be assayed.

14. The method of assay according to claim 2, wherein the assay is conducted without diluting the sample containing the antigen to be assayed.

15. The method of assay according to claim 3, wherein the assay is conducted without diluting the sample containing the antigen to be assayed.

16. The method of assay according to claim 7, wherein the assay is conducted without diluting the sample containing the antigen to be assayed.

17. The method of assay according to claim 10, wherein the assay is conducted without diluting the sample containing the antigen to be assayed.

* * * * *